US010441744B2

(12) United States Patent
Ouyang

(10) Patent No.: US 10,441,744 B2
(45) Date of Patent: Oct. 15, 2019

(54) FLUSHABLE CATHETER AFFIXED TO A WASH LINE ACTIVATED BY A MICROFLUIDIC PRESSURE SWITCH

(71) Applicant: Yannan Ouyang, Memphis, TN (US)

(72) Inventor: Yannan Ouyang, Memphis, TN (US)

( * ) Notice: Subject to any disclaimer, the term of this patent is extended or adjusted under 35 U.S.C. 154(b) by 567 days.

(21) Appl. No.: 14/760,792

(22) PCT Filed: May 12, 2014

(86) PCT No.: PCT/US2014/037635
§ 371 (c)(1),
(2) Date: Jul. 14, 2015

(87) PCT Pub. No.: WO2014/186252
PCT Pub. Date: Nov. 20, 2014

(65) Prior Publication Data
US 2015/0343170 A1 Dec. 3, 2015

Related U.S. Application Data

(60) Provisional application No. 61/822,761, filed on May 13, 2013.

(51) Int. Cl.
*A61M 25/00* (2006.01)
*A61M 39/22* (2006.01)
(Continued)

(52) U.S. Cl.
CPC .......... *A61M 25/00* (2013.01); *A61M 25/003* (2013.01); *A61M 25/0017* (2013.01);
(Continued)

(58) Field of Classification Search
CPC .... A61M 39/16; A61M 39/22; A61M 39/225; A61M 39/227; A61M 39/24;
(Continued)

(56) References Cited

U.S. PATENT DOCUMENTS 4,227,533 A * 10/1980 Godfrey ............ A61M 25/0075
604/247
4,721,123 A 1/1988 Cosentino et al. ......... 134/57 R
(Continued)

FOREIGN PATENT DOCUMENTS

EP 1854502 B1 3/2010

OTHER PUBLICATIONS

Donlan, Rodney M. "Biofilm Elimination on Intravascular Catheters; Important Considerations for the Infectious Disease Practitioner". Clinical Infectious Diseases 2011:52. Apr. 15. 1038-1045.*
(Continued)

*Primary Examiner* — Bhisma Mehta
*Assistant Examiner* — Larry R. Wilson
(74) *Attorney, Agent, or Firm* — VeritayGroup IP; Susan B Fentress

(57) ABSTRACT

This invention relates to systems for delivering medical devices, as well as related systems and methods. The invention also relates to methods of prevention and treatment of biofilm related contamination of systems or devices for medication delivery and methods of treating medical devices, such as catheters, to prevent infection from said device.

6 Claims, 7 Drawing Sheets

(51) Int. Cl.
    *A61M 39/24*   (2006.01)
    *C11D 3/386*   (2006.01)
    *C11D 3/48*    (2006.01)
    *C11D 11/00*   (2006.01)
    *A61L 2/18*    (2006.01)

(52) U.S. Cl.
    CPC ............ *A61M 39/22* (2013.01); *A61M 39/24* (2013.01); *C11D 3/386* (2013.01); *C11D 3/48* (2013.01); *C11D 11/0023* (2013.01); *A61L 2/18* (2013.01); *A61L 2202/14* (2013.01); *A61L 2202/24* (2013.01); *A61M 2025/0019* (2013.01); *A61M 2025/0031* (2013.01)

(58) Field of Classification Search
    CPC ........................ A61M 2039/2406–242; A61M 2039/2473–2486; A61M 25/003; A61M 25/0074; A61M 25/0075; A61M 2025/0019; A61M 2025/0031; A61M 2025/0076; A61M 2025/0002; A61M 2025/0003; A61M 2025/0037–004; A61M 2025/0078; A61M 39/228; A61M 2039/0018; A61M 2039/267; A61M 2039/268; A61M 2205/3337
    See application file for complete search history.

(56) References Cited

U.S. PATENT DOCUMENTS

| | | | | |
|---|---|---|---|---|
| 5,310,524 | A * | 5/1994 | Campbell | A61L 2/00 134/166 C |
| 6,448,062 | B1 * | 9/2002 | Huth | A61L 2/18 435/264 |
| 7,393,501 | B2 | 7/2008 | Zumeris et al. | 422/20 |
| 7,572,439 | B2 | 8/2009 | Kokai-Kun et al. | 424/94.6 |
| 2007/0161949 | A1 | 7/2007 | Knox et al. | 604/93.01 |
| 2008/0281250 | A1 | 11/2008 | Bergsneider et al. | 604/9 |
| 2011/0034986 | A1 | 2/2011 | Chou et al. | 604/9 |
| 2011/0213340 | A1 | 9/2011 | Howell et al. | 604/533 |

OTHER PUBLICATIONS

Donlan, Rodney M. "Biofilm Elimination on Intravascular Catheters; Important Considerations for the Infectious Disease Practitioner". Clinical Infectious Diseases 2011: 52. Apr. 15. 1038-1045. (Year: 2011).*

Betjes, M. G. H. (2011) "Prevention of catheter-related bloodstream infection in patients on hemodialysis," *Nature Reviews Nephrology* 7(5), 257-265.

Blot, S. I. et al. (2005) "Clinical and Economic Outcomes in Critically Ill Patients with Nosocomial Catheter-Related Bloodstream Infections," *Clinical Infectious Diseases* 41(11), 1591-1598.

Cheung, G. Y. et al. (2010) "Understanding the significance of *Staphylococcus epidermidis* bacteremia in babies and children," *Current Opinion in Infectious Diseases* 23(3), 208-216.

Donlan, R. M. (2011) "Biofilm Elimination on Intravascular Catheters: Important Considerations for the Infectious Disease Practitioner," *Clinical Infectious Diseases* 52(8), 1038-1045.

Druce, J. D. et al. (2005) "Cleaning and Sterilization Protocol for Reused Cardiac Electrophysiology Catheters Inactivates Hepatitis and Coxsackie Viruses," *Infection Control and Hospital Epidemiology* 26(8), 720-725.

Hall-Stoodley, L. et al. (2004) "Bacterial biofilms: from the Natural environment to infectious diseases," *Nature Reviews Microbiology* 2(2), 95-108.

Maki, D. G. et al. (2006) "The Risk of Bloodstream Infection in Adults with Different Intravascular Devices: A Systematic Review of 200 Published Prospective Studies," *Mayo Clinic Proceedings* 81(9), 1159-1171.

O'Grady, N. P. et al. (2011) "Guidelines for the Prevention of Intravascular Catheter-related Infections," *Clinical Infectious Diseases* 52(9), e162-e193.

Ouyang, Y. et al. (1997) "Visualization of the distribution of autophosphorylated calcium/calmodulin-dependent protein kinase II after tetanic stimulation in the CA1 area of the hippocampus," *Journal of Neuroscience* 17(14), 5416-5427.

Penna, T. C. V. P. et al. (2000) "Cleaning of Blood-Contaminated Reprocessed Angiographic Catheters and Spinal Needles," *Infection Control and Hospital Epidemiology* 21(8), 499-504.

Renaud, B. et al. (2001) "Outcomes of Primary and Catheter-related Bacteremia: A Cohort and Case—Control Study in Critically Ill Patients," *American Journal of Respiratory and Critical Care Medicine* 163(7), 1584-1590.

Vickery, K. et al. (2004) "Removal of biofilm from endoscopes: evaluation of detergent efficiency," *American Journal of Infection Control* 32(3), 170-176.

Warren, D. K. et al. (2006) "Attributable cost of catheter-associated bloodstream infections among intensive care patients in a nonteaching hospital," *Crititical Care Medicine* 34(8), 2084-2089.

PCT International Search Report of International Application No. PCT/US2014/037635 dated Dec. 1, 2014.

* cited by examiner

FLUSHABLE CATHETER AFFIXED TO A WASH LINE ACTIVATED BY A MICROFLUIDIC PRESSURE SWITCH

CROSS-REFERENCE TO RELATED APPLICATIONS

The present application claims the benefit of U.S. Provisional Patent Application No. 61/822,761, filed on. May 13, 2013, which is incorporated herein by reference.

FIELD OF THE INVENTION

This invention relates to systems for delivering medical devices, as well as related systems and methods. The invention also relates to methods of prevention and treatment of biofilm related contamination of systems or devices for medication delivery and methods of treating medical devices, such as catheters, to prevent infection from said device.

BACKGROUND OF THE INVENTION

Catheter associated infections are a significant percentage of hospital associated infections and pose a major infection threat to those who regularly use catheters in medical treatment. Many catheter-associated infections are related to the growth and contamination by biofilms that may grow inside the catheter device. Therefore, there is a continued need for catheters, kits, and methods to reduce the catheter-associated infections, particularly related to biofilm contamination from the catheter.

SUMMARY OF THE INVENTION

This invention relates to systems for delivering medical devices, as well as related systems and methods. The invention also relates to methods of prevention and treatment of biofilm related contamination of systems or devices for medication delivery and methods of treating medical devices, such as catheters, to prevent infection from said device.

In one embodiment, the present invention contemplates a washable catheter affixed to a flushing line activated by a microfluidic pressure switch. In one embodiment, the catheter is designed to prevent bacteria/biofilm contamination without even a minimal introduction of contaminated fluids with bioactive agents into the blood stream of patients. In one embodiment, the catheter is specifically designed to be reused. In one embodiment, a fluidic pressure switch is provided close to the distal end part of the catheter in proximity of the blood vessel. In one embodiment, when activated through the flushing line, the pressure switch closes access to the distal end of the catheter and allows the flow of fluid from the flushing line through into the central line. In one embodiment, cleaning reagents may then be used to eliminate any biofilm which may have developed in the catheter central line or flushing line. In one embodiment, the present invention contemplates a reagent kit designed for use with the catheter with the microfluidic pressure switch. In one embodiment, the reagents are able to detach cells and proteins attached to plastic surface better than pure bleach. In one embodiment, a specific protocol for cleaning that includes exposure to trypsin, a calcium deficient high ion concentration buffer, and 70% ethanol before flushing and normalization with saline solution.

In one embodiment, the invention contemplates an implantable medical device comprising a catheter with a central line, a flushing line and a distal end microfluidic pressure switch valve. In one embodiment, said catheter comprises a central venous catheter.

In one embodiment, the invention contemplates a kit comprising the device described above and cleaning reagents. In one embodiment, said cleaning reagents comprise: a) digestive enzyme solution, b) calcium deficient buffer with high ion concentration, c) a solution comprising 70% ethanol, and d) physiological saline solution. In one embodiment, said digestive enzyme solution contains trypsin. In one embodiment, said calcium deficient buffer with high ion concentration contains EDTA.

In one embodiment, the invention contemplates a method of decreasing accumulated materials within fluid conduit of a central line of an implanted medical device without contamination comprising, providing: a) a device as described above, and b) a fluid comprising a series of cleaning reagents, wherein said fluid is introduced into said flushing line and said fluid triggers said distal end microfluidic pressure switch valve closing the distal end of the device and said fluid subsequently flows out the central line, and said fluid acts to decrease materials accumulated within said fluid conduit. In one embodiment, said cleaning reagents comprise: a) digestive enzyme solution, b) calcium deficient buffer with high ion concentration, c) a solution comprising 70% ethanol, and d) physiological saline solution. In one embodiment, said method further comprises: a) filling said device via said flushing line with said digestive enzyme solution and incubation for 5-20 min at 37° C., b) flushing said device through said flushing line with said calcium deficient buffer with high ion concentration, c) flushing said device through said flushing line with said solution comprising 70% ethanol, and d) rinsing said device through said flushing line with normal physiological saline solution. In one embodiment, decreasing materials comprises removing said materials. In one embodiment, said method reduces bloodstream infections. In one embodiment, said fluid conduit of an implantable medical comprises an orifice of said device. In one embodiment, said method is performed by an automated system.

In one embodiment, the invention contemplates a medical device comprising a catheter with a central line, a flushing line and a distal end microfluidic pressure switch valve. In one embodiment, the invention contemplates a kit comprising the device described above and cleaning reagents. In one embodiment, said cleaning reagents comprise: a) digestive enzyme solution, b) calcium deficient buffer with high ion concentration, c) a solution comprising 70% ethanol, and d) physiological saline solution. In one embodiment, said digestive enzyme solution contains trypsin. In one embodiment, said calcium deficient buffer with high ion concentration contains a chelating agent.

In one embodiment, the invention contemplates a method of decreasing accumulated materials within fluid conduit of a central line of a medical device without contamination comprising, providing a) a device as described above, and b) a fluid comprising a series of cleaning reagents, wherein said fluid is introduced into said flushing line and said fluid triggers said distal end microfluidic pressure switch valve closing the distal end of the device and said fluid subsequently flows out the central line, and said fluid acts to decrease materials accumulated within said fluid conduit. In one embodiment, said cleaning reagents comprise: a) digestive enzyme solution, b) calcium deficient buffer with high ion concentration, c) a solution comprising 70% ethanol, and d) physiological saline solution.

In one embodiment, the invention contemplates a device to minimize blood contact with the lumen of potentially contaminated catheters is to add a flushing line that is connected to the central catheter line via a microfluidic pressure switch (see FIG. 1, FIG. 2, FIG. 3, FIG. 4, FIG. 5, and FIG. 6). In one embodiment, the switch opens the connection between the flushing line and the central line while blocking access to the bloodstream. As such almost all of the catheter lumen can be filled with a solution to clean and kill bacterial without the risk of introducing the cleaning agents directly into the blood stream. In one embodiment, this device would make flushing and disinfecting catheters safer and may also extend the useful life of the inserted catheters.

In one embodiment, an embodiment of the invention is shown in FIG. 1 in the form of a catheter 1. FIG. 1A: The central line 4 is connected to the flushing line 5, the distal end of the catheter which contains the line to the subject 6 that would enter the blood stream is not connected with the pressure switch 3 engaged. FIG. 1B: This shows a close view of the valve 2. In the closer view of the pressure switch 3, the switch 3 has been engaged and the flushing line 5 is then connected to the central line 4. FIG. 1C: The central line 4 is connected to the distal end of the catheter which contains the line to the subject 6 that would enter the blood stream with the pressure switch 3 is disengaged. The flushing line 5 is closed off. In one embodiment, an embodiment of the invention is shown in FIG. 2 shows a catheter 1 wherein the valve 2 and pressure switch 3 are at an angle relative to the central line 4, flushing line 5, and line to subject 6. In this catheter design, the central line 4 and the flushing line 5 are parallel. In one embodiment, the angled switch 3 allows for a metal guide wire to go straight through the catheter, including the switch which is needed for catheters implanted in a subject. FIG. 2A shows the switch 3 in a position allowing the central line 4 to connect fluidically with the line to subject 6. The arrow indicates flow. FIG. 2B shows the switch 3 in a position allowing the flushing line 5 to connect fluidically with the central line 4. The arrow indicates flow. In one embodiment, an embodiment of the invention is shown in FIG. 3 where several parts of the catheter compared to a standard Y connection version of a standard catheter. Here the valve 2 has the switch 3 engaged which connects the flushing line 5 and the central line 4 and closing off the line to the subject 6. In one embodiment, an embodiment of the invention is shown in FIG. 4 is the catheter in washing mode. In one embodiment, an embodiment of the invention is shown in FIG. 5 is the regular use of the catheter. In one embodiment, an embodiment of the invention is shown in FIG. 6 is the catheter in washing mode. Fluid now flows from the flushing line 5 through the central line 4 in the opposite direction of standard flow from the central line 4.

In principle, the application of the microfluidic pressure switch is safe, reliable and relatively low cost. The best safety property may be that the isolation of wash solution and blood stream remains intact even if the switch stops working. When the catheters need to be cleaned or washed, the solution can be injected into the wash/flushing line. Pressure will push down the valve/cylinder to cut off the connection to blood stream and open the line in the catheter to wash solution. The used wash solution can be released from the central line when the switch is disengaged. A multi-step cleaning kit has been designed for regular use to clean catheters effectively (better than pure bleach) and cost efficiently. Additionally, a machine may be used to facilitate the cleaning of the catheter, such as shown in FIG. 7.

In one embodiment, an embodiment of the invention is shown in FIG. 7 is a system which can be integrated with the catheter to facilitate catheter cleaning steps as previously described. In one embodiment, an embodiment of the invention is a system for cleaning a catheter comprising: a) an implantable medical device comprising a catheter with a central line, a flushing line and a distal end microfluidic pressure switch valve; b) a system line comprising a lumen; c) a control unit; d) at least one cleaning reagent or solution; e) at least one pump; f) at least one fluid pressure sensor; g) temperature regulator; and h) at least one temperature sensor; wherein said catheter is in fluid communication through said system line, wherein said system line is physically connected to said temperature regulator and at least one pump, wherein at least one temperature sensor is in electronic communication with said control unit, wherein at least one pressure sensor is in electronic communication with said control unit, wherein at least one pump is in electronic communication with said control unit, wherein said temperature regulator is in electronic communication with said control unit, and wherein said system line is in fluid communication with at least one cleaning reagent. In one embodiment, said system line connects to the flushing line of said catheter. In one embodiment, said system will turn off said pumps if at least one pressure sensor indicates that the fluid pressure is beyond safety levels. In one embodiment, aid the temperature of fluid passing through said system line to said catheter is regulated by said control unit through said temperature regulator with feedback from at least one temperature sensor. In one embodiment, said temperature is physiological temperature of 37° C. In one embodiment, said control unit is mechanically connected to said pump and said temperature regulator. In one embodiment, said control unit is electronically connected to said pump and said temperature regulator. The system comprises a control unit 12 that may electronically and/or mechanically control several aspects including the delivery of each of the different solutions 8 via the pump 11 and a sensor 10, which measures the fluid pressure. If the sensor 10 indicates that the fluid pressure is beyond safety levels, the pump 11 will be shut down via the control unit 12. The temperature of the delivered solutions may be regulated by the temperature regulator/water bath 9 that could adjust the temperature for example to a physiological temperature of 37° C.

Much research has focused on treatment of biofilm, a late stage of accumulation of bacterial and other pathogens in catheters. However, reducing possibility of accumulation of bacterial inside the tubes of catheters may be a more effective, preventive approach to abridge infection. This may be particularly practical with use of the washable catheter of the current invention and the following four steps kit to regularly clean the catheter of the current invention.

In one embodiment, the invention contemplates a four step wash protocol to clean catheters that may be contaminated by bacterial (even accumulated biofilm) to avoid infection, such as in a clinical setting. The four step wash protocol, in some embodiments, may involve a kit comprising solutions A, B, C and D as previously described. In one embodiment, the completion time for the procedure may be approximately 50 minutes. In some embodiments, the procedure may require less than 50 minutes. One embodiment of the method of catheter cleaning is as follows: Step 1. Fill the catheter with solution A (1× trypsin-EDTA and may add other proteases if necessary) and keep for 20 min (time may be modified depending on the possibility of contamination or period since last wash) at 37° C. to digest proteins to release possible bacterial and other cells and proteins from plastic surface. Step 2. Wash with solution B (for example, Hank's buffer without calcium and magnesium but with additional 0.45M NaCl or other high ion concentration (greater than 2% weight/volume)) that deactivate trypsin and may also wash off attached proteins and bacterial (10 minutes). Step 3. Treat catheters with solution C (70% ethanol) that may denature remaining protein and bacterial still attached on plastics (10 minutes). Step 4. Rinse with solution D (physiological saline) to wash off any remaining debris and to bring the catheter back to normal physiological condition and so as to be ready for clinical applications (10 minutes). In one embodiment, the invention relates to a catheter cleaning system (with a pump to control pressure and wash speed and switches to change solutions smoothly). On example of such a system is shown in FIG. 7.

In one embodiment, the present invention contemplates a washable catheter affixed to a flushing line activated by a microfluidic pressure switch. In one embodiment, the catheter is designed to prevent bacteria/biofilm contamination without even a minimal introduction of contaminated fluids with bioactive agents into the body of patients. In one embodiment, the catheter is specifically designed to be reused. In one embodiment, the catheter is a urinary catheter. In one embodiment, said microfluidic pressure switch is added to the tip of a regular urinary catheter. In one embodiment, said flushing line is inside of the central line of said catheter. In one embodiment, said microfluidic pressure switch further comprises a head attached to at least one cross connecting feature which is engaged with the flushing line. In one embodiment, said microfluidic pressure switch is engaged with the central line through at least one connecting feature. In one embodiment, a fluidic pressure switch is provided close to the tip end part of the catheter in proximity of the bladder or end of the urethra. In one embodiment, when engaged through the flushing line, the pressure switch closes access to the distal end of the catheter and allows the flow of fluid from the flushing line through into the central line. In one embodiment, cleaning reagents may then be used to eliminate any biofilm which may have developed in the catheter central line or flushing line. When the catheter is regularly used to release urine, the microfluidic pressure switch is not engaged; when the catheter is being washed/cleaned, the cleaning solution will be injected through the flushing line and the pressure will push the switch up to block the connection from the central line to the body and washing solution will go backward out body through the regular tube out of the central line. The center part of the microswitch is attached to the out switch tube with a cross like connection part that allows solution to flow out (see FIG. 8A, FIG. 8B, FIG. 8C and FIG. 8D). In one embodiment, the present invention contemplates a reagent kit designed for use with the catheter with the microfluidic pressure switch. In one embodiment, the reagents are able to detach cells and proteins attached to plastic surface better than pure bleach. In one embodiment, a specific protocol for cleaning that includes exposure to trypsin, a calcium deficient high ion concentration buffer, and 70% ethanol before flushing and normalization with saline solution. FIG. 8A-D show one embodiment of the device wherein said device can be used as a urinary catheter. FIG. 8A shows the microfluidic pressure switch 3 attached to the end of a the flushing line 5 and within the urinary catheter (which serves as a central line 4). In this arrangement, the valve 2 is attached within the end of the flushing line 5 and is engaged on the outside with the central line 4 with an bracing structure 14 but one that allows the passage of fluid through the central line 4. The microfluidic pressure switch 3 is also attached to internal bracing features 15. The bracing features are attached by at least one central rod 16 to the tip of the pressure switch 3. FIG. 8B shows the microfluidic pressure switch 3 is half way engaged by the flow of fluid through the flushing line 5. FIG. 8C shows the pressure switch fully engaged where the microfluidic pressure switch 3 is moved forward to block the narrowed portion 13 of the central line. Parts 15 and 3 are one piece attached by at least one rod 16 and move together in a vertical manner. When washing, fluid is pushed through the flushing line, fluidic pressure will push the bracing features 15 to hold the pressure switch tip 3 in place to cut off the connection from washing solution to body (narrowed portion 13 of the central line). This narrowed portion 13 may also be the end of the central line that is engaged with a subject. FIG. 8D shows the microfluidic pressure switch 3 and valve 2 not attached to the central line or interfaced with the catheter.

In one embodiment, the invention contemplates an implantable medical device comprising a catheter with a central line, a flushing line and a distal end microfluidic pressure switch valve. In one embodiment, said flushing line is inside of the central line of said catheter. In one embodiment, said microfluidic pressure is on the tip of said catheter. In one embodiment, said catheter comprises a urinary catheter. In one embodiment, the invention contemplates a kit comprising the device described above and cleaning reagents. In one embodiment, said cleaning reagents comprise: a) digestive enzyme solution, b) calcium deficient buffer with high ion concentration, c) a solution comprising 70% ethanol, and d) physiological saline solution. In one embodiment, said digestive enzyme solution contains trypsin. In one embodiment, said calcium deficient buffer with high ion concentration contains EDTA. In one embodiment, the invention contemplates a method of decreasing accumulated materials within fluid conduit of a central line of a urinary catheter device without contamination comprising, providing: a) a device as described above, and b) a fluid comprising a series of cleaning reagents, wherein said fluid is introduced into said flushing line and said fluid triggers said distal end microfluidic pressure switch valve closing the distal end of the device and said fluid subsequently flows out the central line, and said fluid acts to decrease materials accumulated within said fluid conduit. In one embodiment, said cleaning reagents comprise: a) digestive enzyme solution, b) calcium deficient buffer with high ion concentration, c) a solution comprising 70% ethanol, and d) physiological saline solution. In one embodiment, said method further comprises: a) filling said device via said flushing line with said digestive enzyme solution and incubation for 5-20 min at 37° C., b) flushing said device through said flushing line with said calcium deficient buffer with high ion concentration, c) flushing said device through said flushing line with said solution comprising 70% ethanol, and d) rinsing said device through said flushing line with normal physiological saline solution. In one embodiment, decreasing materials comprises removing said materials. In one embodiment, said method reduces bloodstream infections. In one embodiment, said method reduces urinary infections. In one embodiment, said method reduces kidney infections. In one embodiment, said fluid conduit of an implantable medical comprises an orifice of said device. In one embodiment, said method is performed by an automated system.

In one embodiment, the invention contemplates a medical device comprising a catheter with a central line, a flushing line and a distal end microfluidic pressure switch valve. In one embodiment, said catheter comprises a central venous catheter. In one embodiment, said catheter comprises a urinary catheter. In one embodiment, said flushing line is inside of the central line of said catheter. In one embodiment, said microfluidic pressure is on the tip of said catheter. In one embodiment, the invention contemplates a kit comprising the device described above and cleaning reagents. In one embodiment, said cleaning reagents comprise: a) digestive enzyme solution, b) calcium deficient buffer with high ion concentration, c) a solution comprising 70% ethanol, and d) physiological saline solution. In one embodiment, said digestive enzyme solution contains trypsin. In one embodiment, said calcium deficient buffer with high ion concentration contains a chelating agent. In one embodiment, the invention contemplates a method of decreasing accumulated materials within fluid conduit of a central line of a medical device without contamination comprising, providing a) a device as described above, and b) a fluid comprising a series of cleaning reagents, wherein said fluid is introduced into said flushing line and said fluid triggers said distal end microfluidic pressure switch valve closing the distal end of the device and said fluid subsequently flows out the central line, and said fluid acts to decrease materials accumulated within said fluid conduit. In one embodiment, said cleaning reagents comprise: a) digestive enzyme solution, b) calcium deficient buffer with high ion concentration, c) a solution comprising 70% ethanol, and d) physiological saline solution.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

Definitions

To facilitate the understanding of this invention, a number of teens are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "implantable medical device" is used throughout the specification to describe implanted medical devices that contain lumens or central cavities that have an interface with a portion of the subject's body, most commonly involving fluid interactions, such as stents, catheters, etc.

As used herein, the term "catheter" is used throughout the specification to describe a thin tube extruded from medical grade materials serving a broad range of functions. Catheters are medical devices that can be inserted in the body to treat diseases or perform a surgical procedure. By modifying the material or adjusting the way catheters are manufactured, it is possible to tailor catheters for cardiovascular, urological, gastrointestinal, neurovascular, and ophthalmic applications. Catheters can be inserted into a body cavity, duct, or vessel. Functionally, they allow drainage, administration of fluids or gases, access by surgical instruments, and also perform wide variety of other tasks depending on the type of catheter. The process of inserting a catheter is catheterization. In most uses, catheter is a thin, flexible tube ("soft" catheter) though catheters are available in varying levels of stiffness depending on the application. A catheter left inside the body, either temporarily or permanently, may be referred to as an indwelling catheter. A permanently inserted catheter may be referred to as a permeath. A range of polymers may be used for the construction of catheters, including, but not limited to, silicone rubber, nitinol, nylon, polyurethane, and polyethylene terephthalate (PETE) latex, and/or thermoplastic elastomers. Silicone may be used as it is considered one of the most common choices because it is inert and unreactive to body fluids and a range of medical fluids with which it might come into contact.

As used herein, the term "central line" is used throughout the specification to describe a lumen containing section of a cather or other medical device, which is the primary path of delivery of a fluid treatment.

As used herein, the term "flushing line or wash line" is used throughout the specification to describe a separate lumen containing path within a medical device, which is not primarily used for the delivery of a fluid treatment, but rather can serve as an avenue to enable treatment of the device itself and potentially access the central line. In preferred embodiments, treatment includes removal, break down, of cellular debris and or sterilization of the internal catheter elements in fluid communication with the flushing line.

As used herein, the term "line to subject" is used throughout the specification to describe the section of the medical device, which serves to directly deliver the fluid treatment to the subject.

As used herein, the term "microfluidic pressure switch valve" is used throughout the specification to describe a valve within a medical device, which may enable the alteration of the path of connectivity of the central line, the flushing line, and the line to the subject. When engaged the path from the central line to the line to subject is altered to connect only the central line to the flushing line. In one embodiment, the switch within the valve is sensitive to pressure applied from the flushing line, enabling the switch to engage or disengage. In one embodiment, the microfluidic pressure switch may also contain a magnetic element to aid in the adjustment of said switch in the valve.

As used herein, the term "digestive enzyme" is used throughout the specification to describe enzymes that break down polymeric macromolecules into their smaller building blocks. Digestive enzymes are classified based on their target substrates: proteases and peptidases split proteins into small peptides and amino acids; lipases split fat into three fatty acids and a glycerol molecule; carbohydrates split carbohydrates such as starch and sugars into simple sugars such as glucose; and nucleases split nucleic acids into nucleotides. Digestive enzymes consider all enzymes that can digest the tissue matrixes and/or cell membrane proteins. One specific example of a digestive enzyme is Trypsin. Another exemplary enzyme is papain.

As used herein, the term "calcium deficient buffer with high ion concentration" is used throughout the specification to describe a buffer in which is substantially calcium ion free or contains a calcium sequestering agent, such as a chelating agent like EDTA or EGTA.

As used herein, the term "physiological saline" is used throughout the specification to describe a sterile solution of sodium chloride (NaCl, more commonly known as salt) in water.

As used herein, the term "chelating agent" is used throughout the specification to describe a chemical or set of chemicals, which are used to absorb or sequester metal ions. Specific examples of chelating agents include EDTA and EGTA.

As used herein, the term "ethylenediaminetetraacetic acid" or "EDTA" is used throughout the specification to describe a hexadentate ligand and chelating agent with the structure:

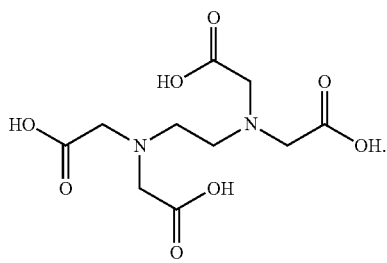 [SMILES: O=C(O)CN(CCN(CC(=O)O)CC(=O)O)CC(=O)O]

As used herein, the term "ethylene glycol tetraacetic acid" or "EGTA" is used throughout the specification to describe a hexadentate ligand and chelating agent with the structure:

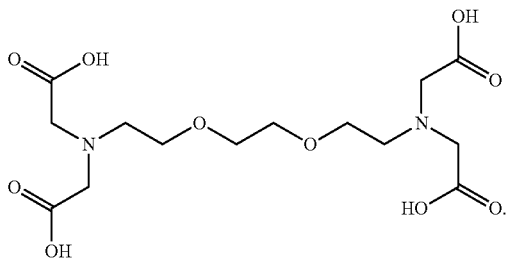 [SMILES: O=C(O)CN(CCOCCOCCN(CC(=O)O)CC(=O)O)CC(=O)O]

As used herein, the term "biofilm" is used throughout the specification to describe any group of microorganisms in which cells stick to each other on a surface. These adherent cells are frequently embedded within a self-produced matrix of extracellular polymeric substance (EPS). Biofilm EPS, which is also referred to as slime (although not everything described as slime is a biofilm), is a polymeric conglomeration generally composed of extracellular DNA, proteins, and polysaccharides. Biofilms may form on living or non-living surfaces and can be prevalent in natural, industrial and hospital settings [1].

As used herein, the term "bloodstream infections" or "bacteremia" is used throughout the specification to describe presence of bacteria in the blood and the possible resulting infection. The blood is normally a sterile environment, so the detection of bacteria in the blood (most commonly accomplished by blood cultures) is always abnormal. Bacteria can enter the bloodstream as a severe complication of infections (like pneumonia or meningitis), during surgery (especially when involving mucous membranes such as the gastrointestinal tract), or due to catheters and other foreign bodies entering the arteries or veins (including intravenous drug abuse).

As used herein, the term "prevention" or "preventing" is used throughout the specification to describe: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The present invention contemplates the above-described compositions in "therapeutically effective amounts" or "pharmaceutically effective amounts", which means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

As used herein, the term "subject" is used throughout the specification to describe to any mammal, preferably a human patient, livestock, or domestic pet.

In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 1A: The central line 4 is connected to the flushing line 5, the distal end of the catheter which contains the line to the subject 6 that would enter the blood stream is not connected with the pressure switch 3 engaged. FIG. 1B: This shows a close view of the valve 2. In the closer view of the pressure switch 3, the switch 3 has been engaged and the flushing line 5 is then connected to the central line 4. FIG. 1C: The central line 4 is connected to the distal end of the catheter which contains the line to the subject 6 that would enter the blood stream with the pressure switch 3 is disengaged. The flushing line 5 is closed off.

FIG. 2A shows the switch 3 in a position allowing the central line 4 to connect fluidically with the line to subject 6. The arrow indicates flow. FIG. 2B shows the switch 3 in a position allowing the flushing line 5 to connect fluidically with the central line 4. The arrow indicates flow.

FIG. 8A shows the microfluidic pressure switch 3 attached to the end of a the flushing line 5 and within the urinary catheter (which serves as a central line 4). In this arrangement, the valve 2 is attached within the end of the flushing line 5 and is engaged on the outside with the central line 4 with an bracing structure 14 but one that allows the passage of fluid through the central line 4. The microfluidic pressure switch 3 is also attached to internal bracing features 15. The bracing features are attached by at least one central rod 16 to the tip of the pressure switch 3. FIG. 8B shows the microfluidic pressure switch 3 is half way engaged by the flow of fluid through the flushing line 5. FIG. 8C shows the pressure switch fully engaged where the microfluidic pressure switch 3 is moved forward to block the narrowed portion 13 of the central line. Parts 15 and 3 are one piece attached by at least one rod 16 and move together in a vertical manner. When washing, fluid is pushed through the flushing line, fluidic pressure will push the bracing features 15 to hold the pressure switch tip 3 in place to cut off the connection from washing solution to body (narrowed portion 13 of the central line). This narrowed portion 13 may also be the end of the central line that is engaged with a subject. FIG. 8D shows the microfluidic pressure switch 3 and valve 2 not attached to the central line or interfaced with the catheter.

DESCRIPTION OF THE INVENTION

Background

Catheters have been widely used in clinic for patient long-term care. However, approximately 250,000 to 500,000 catheter-related bloodstream infections occur annually in US hospitals (Maki et al., *Mayo Clin Proc* 2006 81:1159-71) [2]. Catheter-related bloodstream infections have been associated with increases in patient morbidity and mortality, prolonged hospital stay, and increased health care costs (Renaud and Brun-Buisson, *Am J Respir Crit Care Med* 2001 163:1584-90. [3]; Blot et al., *Clin Infect Dis* 2005; 41:1591-8. [4]; Warren et al., *Crit Care Med* 2006 34:2084-9) [5]. Infectious agents can populate the lumen of the catheters and may be forced into the bloodstream as fluids are may be injected into the patient through the catheters. Solving the problem has proven to be a challenge (Betjes, *Nat. Rev. Nephrol.* 2011; 7: 257-265 [6]; Cheung and Otto, *Curr Op in Infect Dis.* 2010 Jun. 23(3): 208-216 [7]; Donlan, *Clinical Infectious Diseases* 2011 52(8):1038-1045) [8].

Majority of catheters used in clinic have an open end to the blood stream to allow intravenous delivery of drugs and nutrition. Current test procedures to wash or clean catheters in situ involve injection of solutions into the catheter followed by lock the tube once it is filled to avoid introduction of cleaning solutions into blood stream (Donlan 2011) [8]. However, even when locked the cleaning solutions may diffuse out of the catheter into blood through the open distal end. Furthermore, cleaning solutions must be sucked out of the catheter at the conclusion of the lock treatment. As cleaning solutions are sucked out of the catheter patient blood will move into the tube and may come in contact with the remains of the cleaning solution that sticks to or attaches to the lumen surface. This may be considered as another source of blood contamination. Therefore, to overcome the difficulties in separating the wash solutions and the blood stream it may be necessary to re-design catheters with this requirement in mind.

One way to minimize blood contact with the lumen of potentially contaminated catheters is to add a flushing line that is connected to the central catheter line via a microfluidic pressure switch (see FIG. 1, FIG. 2, FIG. 3, FIG. 4, FIG. 5, and FIG. 6). The switch opens the connection between the flushing line and the central line while blocking access to the bloodstream. As such almost all of the catheter lumen can be filled with a solution to clean and kill bacterial without the risk of introducing the cleaning agents directly into the blood stream. This device would make flushing and disinfecting catheters safer and may also extend the useful life of the inserted catheters.

Figure 1:
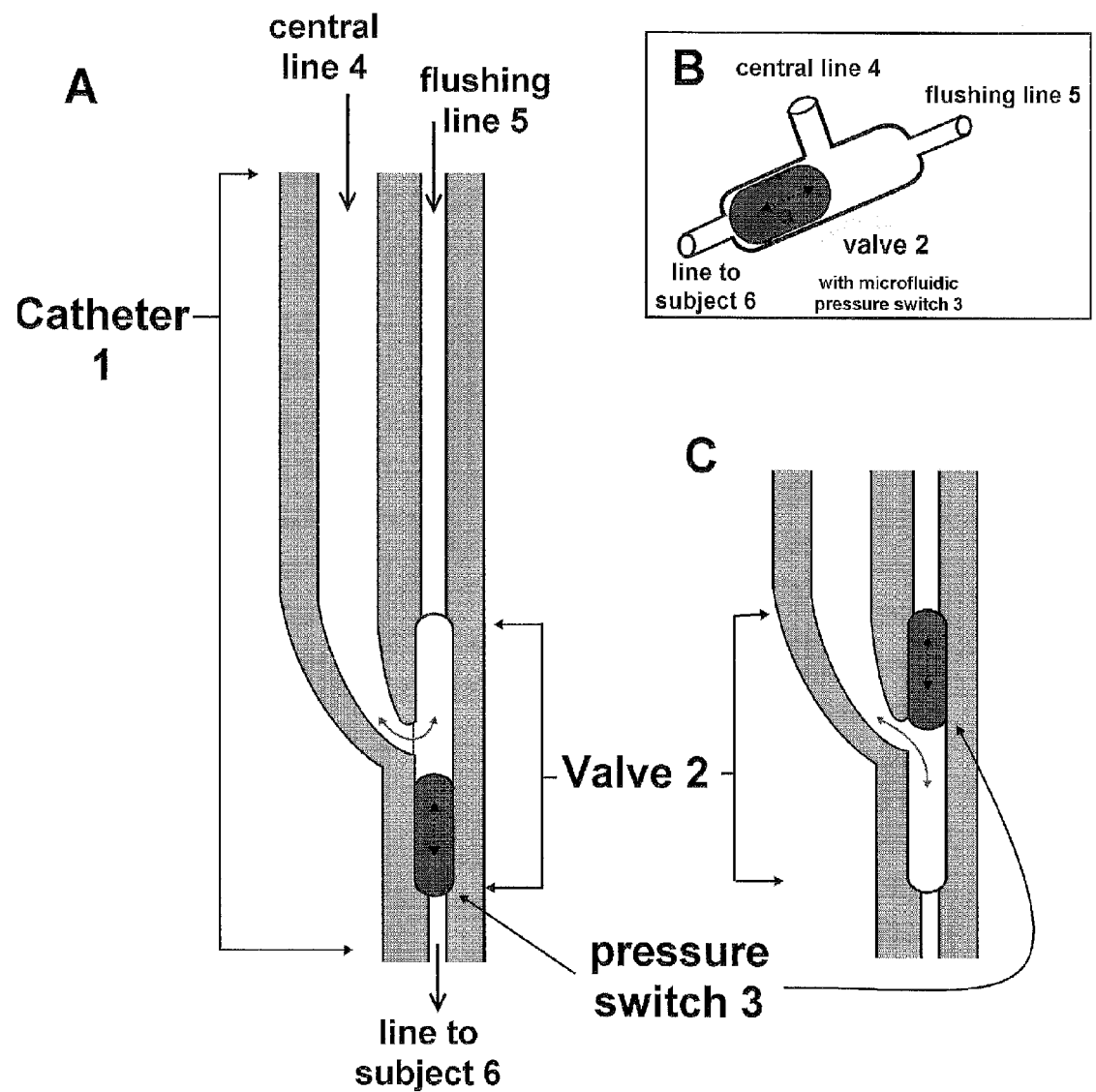
FIG. 1 shows one potential embodiment of the invention in the form of a catheter 1.
Figure 2:
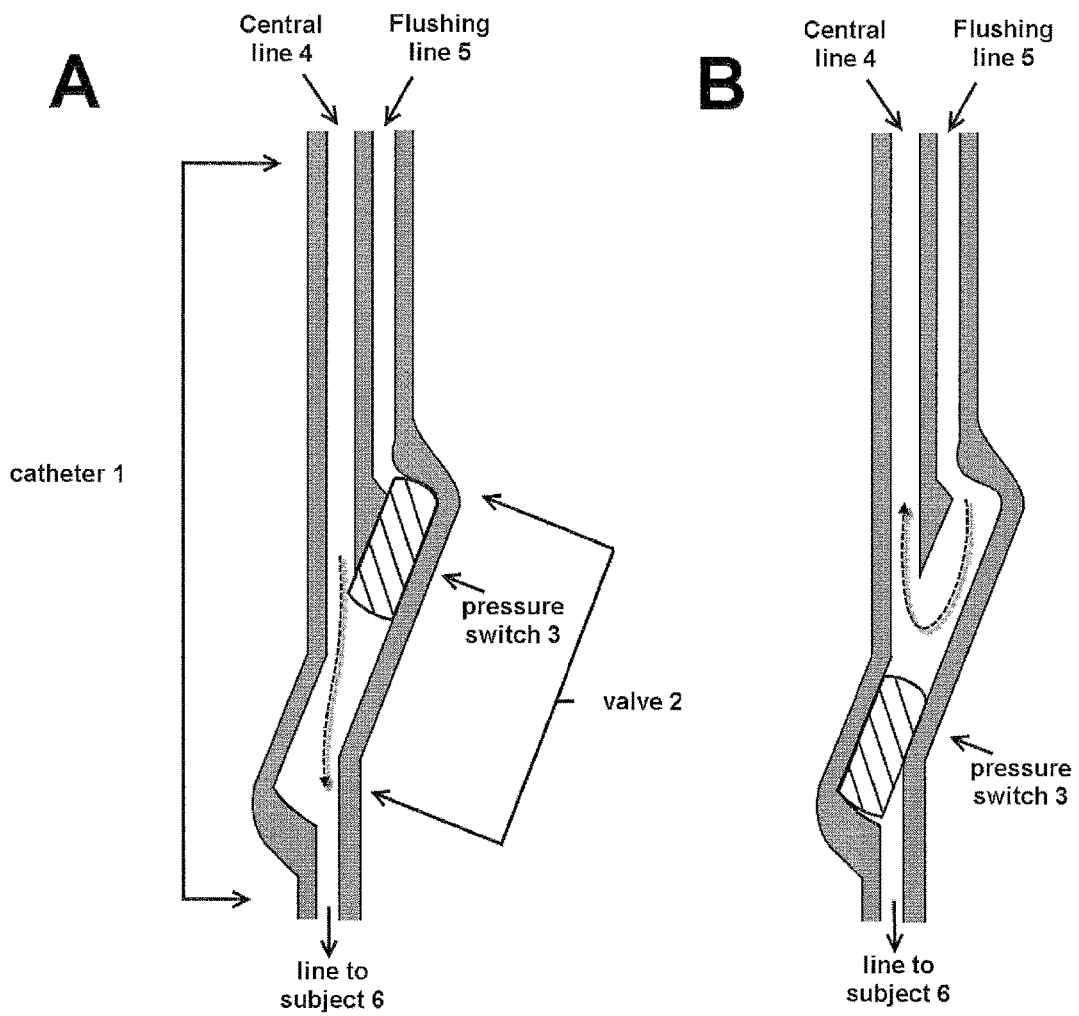
FIG. 2 shows one embodiment of the current invention catheter 1 wherein the valve 2 and pressure switch 3 are at an angle relative to the central line 4, flushing line 5, and line to subject 6. In this catheter design, the central line 4 and the flushing line 5 are parallel. In one embodiment, the angled switch 3 allows for a metal guide wire to go straight through the catheter, including the switch which is needed for catheters implanted in a subject.
Figure 3:
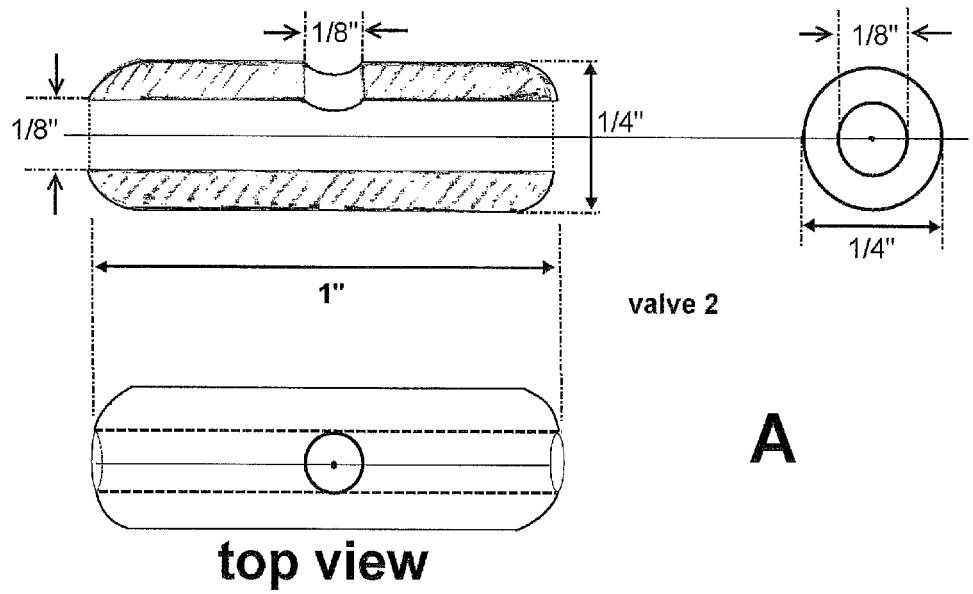
FIG. 3 shows one embodiment of several parts of the catheter compared to a standard Y connection version of a standard catheter. Here the valve 2 has the switch 3 engaged which connects the flushing line 5 and the central line 4 and closing off the line to the subject 6.
Figure 3:
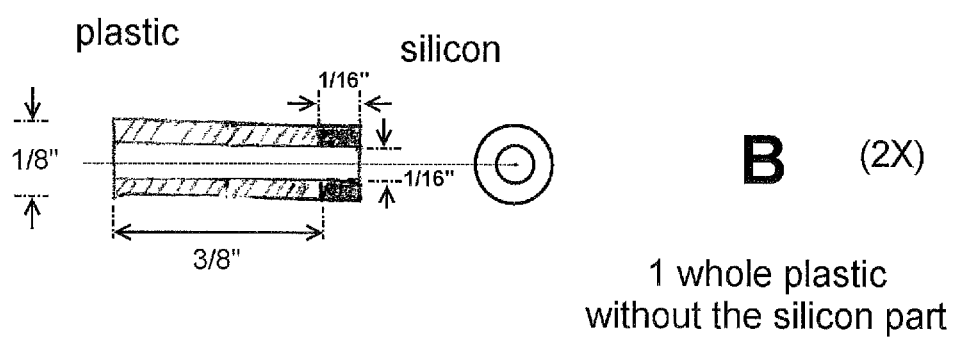
Figure 3:
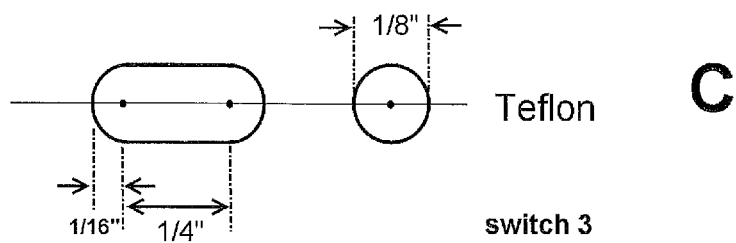
Figure 4:
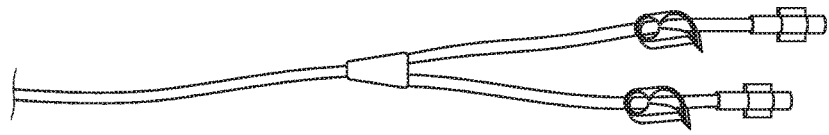
FIG. 4 shows the catheter in washing mode.
Figure 4:
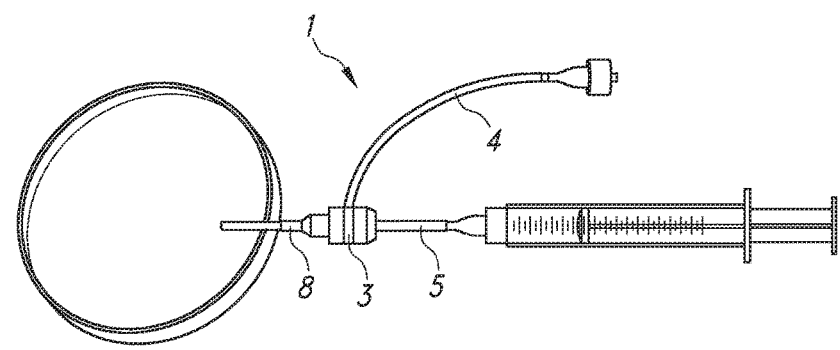
Figure 5:
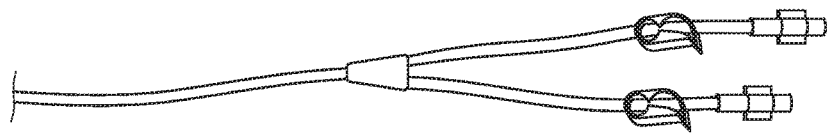
FIG. 5 shows the regular use of the catheter.
Figure 5:
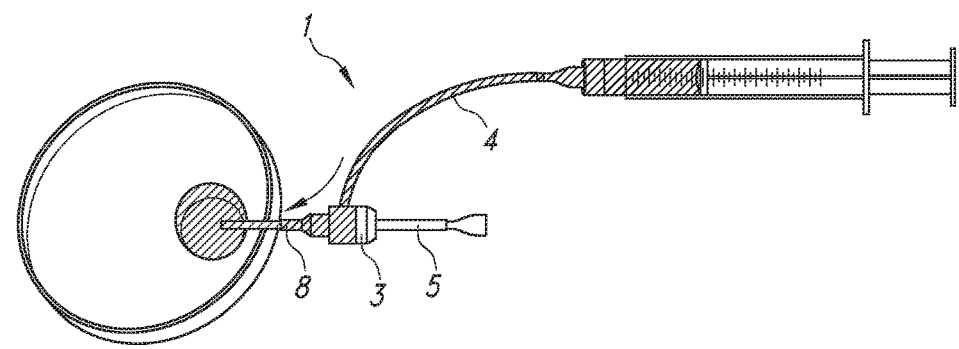
Figure 6:
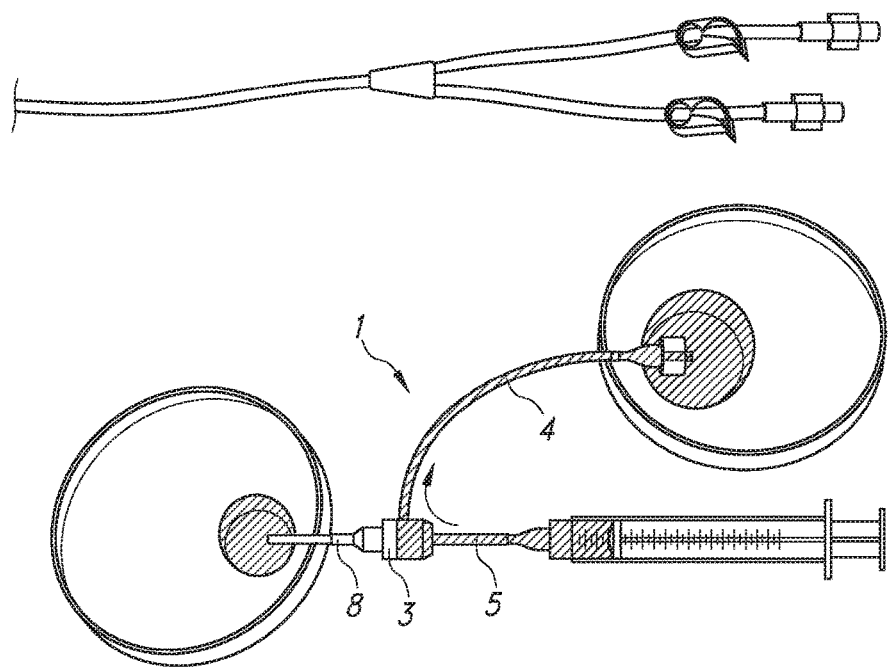
FIG. 6 shows the catheter in washing mode. Fluid now flows from the flushing line 5 through the central line 4 in the opposite direction of standard flow from the central line 4.
Figure 7:
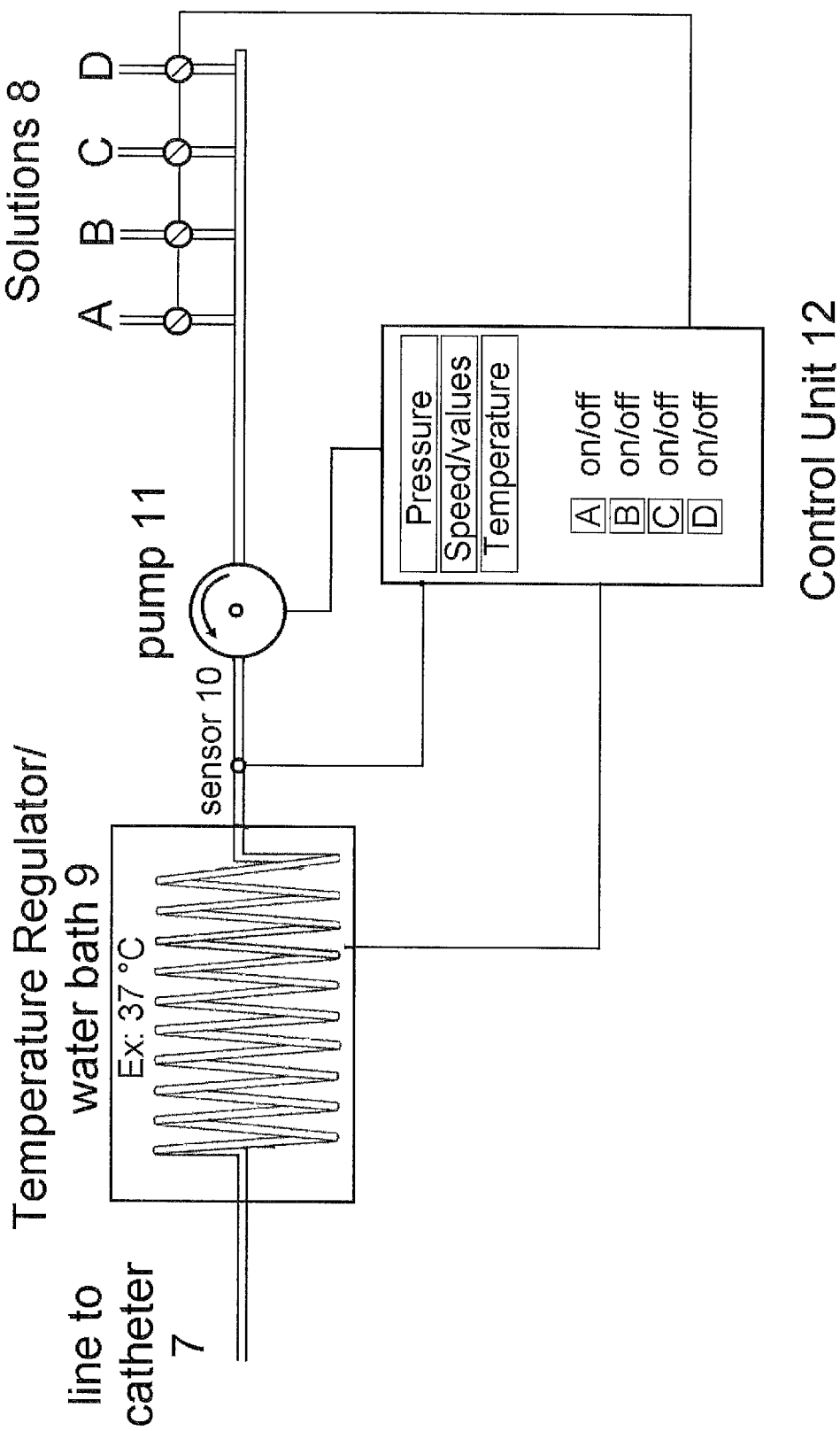
FIG. 7 shows one embodiment of the current invention which contemplates a system which can be integrated with the catheter to facilitate catheter cleaning steps as previously described. The system comprises a control unit 12 that may electronically and/or mechanically control several aspects including the delivery of each of the different solutions 8 via the pump 11 and a sensor 10, which measures the fluid pressure. If the sensor 10 indicates that the fluid pressure is beyond safety levels, the pump 11 will be shut down via the control unit 12. The temperature of the delivered solutions may be regulated by the temperature regulator/water bath 9 that could adjust the temperature for example to a physiological temperature of 37° C.
Figure 8:
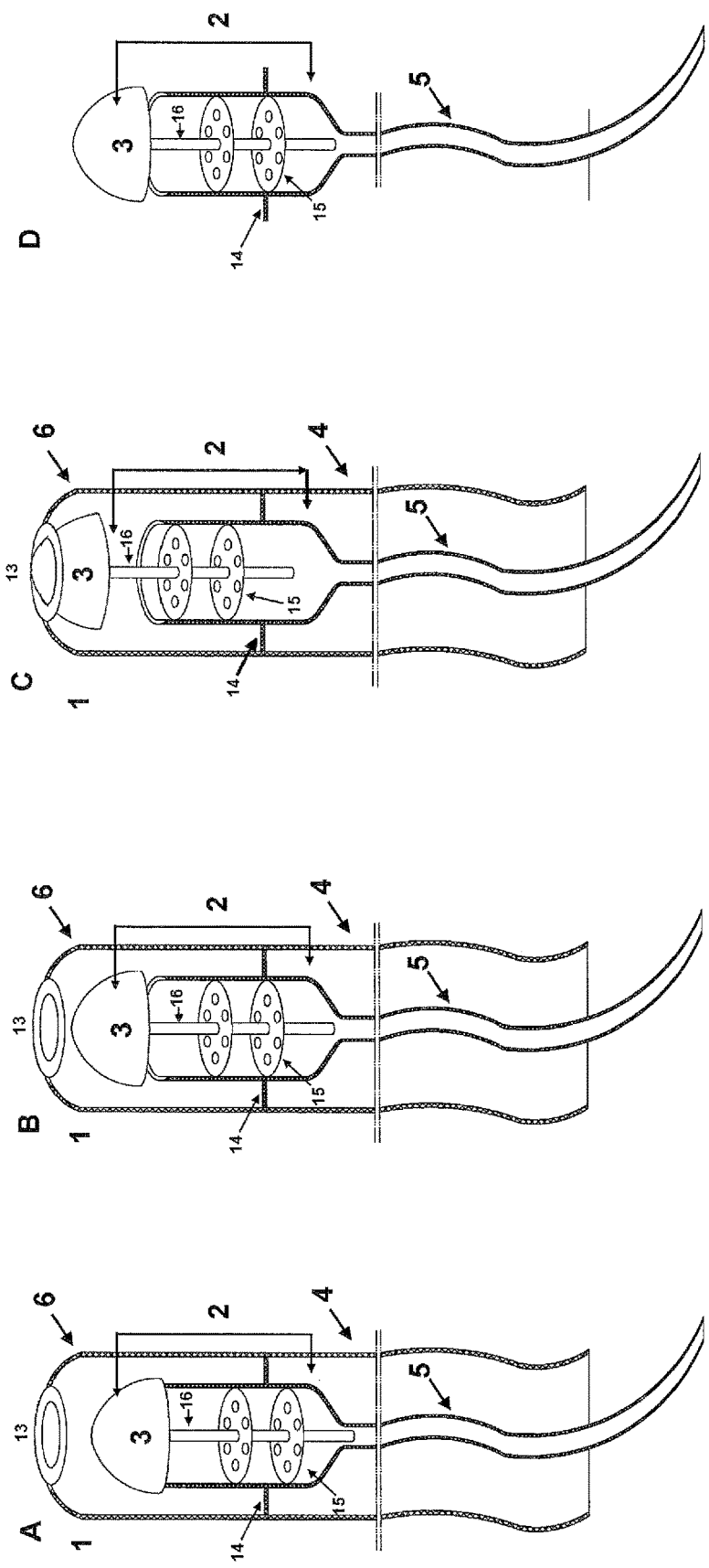
FIG. 8A-D show one embodiment of the device wherein said device can be used as a urinary catheter.

In principle, the application of the microfluidic pressure switch is safe, reliable and relatively low cost. The best safety property may be that the isolation of wash solution and blood stream remains intact even if the switch stops working. When the catheters need to be cleaned or washed, the solution can be injected into the wash/flushing line. Pressure will push down the valve/cylinder to cut off the connection to blood stream and open the line in the catheter to wash solution. The used wash solution can be released from the central line when the switch is disengaged. A multi-step cleaning kit has been designed for regular use to clean catheters effectively (better than pure bleach) and cost efficiently. Additionally, a machine may be used to facilitate the cleaning of the catheter, such as shown in FIG. 7.

Much research has focused on treatment of biofilm, a late stage of accumulation of bacterial and other pathogens in catheters. However, reducing possibility of accumulation of bacterial inside the tubes of catheters may be a more effective, preventive approach to abridge infection. This may be particularly practical with use of the washable catheter of the current invention and the following four steps kit to regularly clean the catheter of the current invention.

Catheter Cleaning Protocols

The first step with solution A: Solution A contains proteases. Proteases can be used to digest proteins attached to plastic surface. For example, trypsin can be used to release a cell layer from plastic dishes. An application of trypsin (pre-warmed at 37° C.) can lead the single cell layer to detach from the plastic bottom in a few minutes. When incubated at 30° C. (may be similar to the temperature of the part of catheters out of body), trypsin may detach heavy, multilayer cells from plastic surface in 30 min. Biofilm often contains multi-layers of cells can be digested and detach the layers of cells from plastic surface 30 min after trypsin incubation at 37° C.

The second step with solution B: While most of the cells may be detached by protease treatment (such as trypsin), a few cells may remain on the plastic surface, particularly when the incubation temperature is not at optimal digestive temperature (such as 37° C. for trypsin) as may happen for the part of catheters out of patients. Solution B may be used to continue the treatment for two purposes. Solution B contains high ion concentration that may reduce attachment of cell to plastic surface at room temperature. High ion concentration such as addition of 0.45M NaCl may also further reduce proteins binding to the surface (Ouyang et al., 1997) [9]. The second purpose is to deactivate remaining trypsin as a buffer without calcium and magnesium. Even with significant number of cells attached initially plastics, a ten minute incubation with solution B may effectively release most of the cells and other remains. The effect is more clearly demonstrated after adding solution C. Although it is not necessary to understand the mechanism of action of the current invention, it is believed that a higher concentration of saline solution (0.45M NaCl or above), similar to elution buffer for ion chromatography, helps to clean cells and/or proteins still attached to plastic due to charge of the ions.

The third step with solution C: After most of the bacterial and cells detach from plastic and wash away, 70% ethanol may be applied to kill possible bacterial remains and/or denature proteins still attached on the plastic surface. This step changes the solution from water phase to ethanol phase and may generate changes that make remains much easier to wash away without additional mechanical force.

Final step with solution D: Regular physiological saline may be applied to wash away ethanol and other possible remains of accumulated materials similar as the phase changes induced with the addition of solution C. However, the main purpose of this step is to normalize the catheter to be ready for clinical purpose. Catheters are well cleaned and safe to use after this stage since several steps are designed to remove proteases and other chemicals potentially harmful for patients.

Although it is not necessary to understand the mechanism of an invention, it is believed that, in some embodiments, the presently disclosed methods and/or kits have an improved cleaning capability when compared to bleach. The treatment protocols described herein have been compared with cells treated with bleach as a control. Bleach can effectively destroy cells but remains of the cells were not easily removed with 2 buffer washes in similar manner as to change from solution A to B and then to C. The cleanness of the plastic surface when the solutions A to C are used is better than that after the bleach treatment and two washes with buffer. The other disadvantage of bleach is that it may interact with the materials made for catheters to change the property and safety to use with patient. In contrast, the solutions used in this kit are not strongly interacted with the materials made for catheters. Therefore, the catheters could be used safely for long-term care.

In contrast with other procedure used in practice or research that may require 8 hours or more in lock mode and possible diffusing contamination with bloodstream (Donlan 2011) [8], one embodiment of the current invention described may provide a safer, more effective, efficient and less expensive alternative. Application of this type of procedure or treatment may reduce catheter related infection significantly therefore avoiding drastic situation for patients who already in challenge condition.

Example Washing Procedure

In one embodiment, the invention contemplates a four step wash protocol to clean catheters that may be contaminated by bacterial (even accumulated biofilm) to avoid infection, such as in a clinical setting. The four step wash protocol, in some embodiments, may involve a kit comprising solutions A, B, C and D as previously described. In one embodiment, the completion time for the procedure may be approximately 50 minutes. In some embodiments, the procedure may require less than 50 minutes. One embodiment of the method of catheter cleaning is as follows:

Step 1. Fill the catheter with solution A (1× trypsin-EDTA and may add other proteases if necessary) and keep for 20 min (time may be modified depending on the possibility of contamination or period since last wash) at 37° C. to digest proteins to release possible bacterial and other cells and proteins from plastic surface.

Step 2. Wash with solution B (for example, Hank's buffer without calcium and magnesium but with additional 0.45M NaCl or other high ion concentration (greater than 2% weight/volume)) that deactivate trypsin and may also wash off attached proteins and bacterial (10 minutes).

Step 3. Treat catheters with solution C (70% ethanol) that may denature remaining protein and bacterial still attached on plastics (10 minutes).

Step 4 Rinse with solution D (physiological saline) to wash off any remaining debris and to bring the catheter back to normal physiological condition and so as to be ready for clinical applications (10 minutes).

In one embodiment, the invention relates to a catheter cleaning system (with a pump to control pressure and wash speed and switches to change solutions smoothly). On example of such a system is shown in FIG. 7.

Catheter-related infections has been identified as a significant problem in the medical field. One reference, Maki, D. G. et al. (2006) *Mayo Clin. Proc.* 81(9), 1159-1171 [2] discloses a study aiming to understand the absolute and relative risks of bloodstream infection (BSI) associated with the various types of intravascular devices (IVDs). The study indicated that a wide variety of intravascular devices present risks of blood infections and suggests greater attention to preventative measures and improved devices are needed, but does not describe any such improvements. This reference does not describe the type of device or cleaning procedures as described in the current invention.

One reference, Renaud, B. and Brun-Buisson, C. (2001) *Am. J. Respir. Crit. Care. Med.* 163(7), 1584-1590 [3], describes a hospital patient study wherein the incidence and outcomes of primary and definite catheter-related bloodstream (CRB) or secondary nosocomial bloodstream infection (NBSI) were evaluated. The reference stressed the need for increased awareness of these infections and recommended a special category for "catheter-related bacteremia." This reference does not describe the type of device or cleaning procedures as described in the current invention.

One reference, Blot, S. I. et al. (2005) *Clin. Infect. Dis.* 41(11), 1591-1598 [4], is a study concludes that catheter-related bloodstream infection was associated with significant excesses in duration of mechanical ventilation, duration of intensive care unit and hospital stays, and a significant increase in total hospital cost. In the presence of prompt catheter removal and initiation of antimicrobial therapy, no significant attributable mortality could be documented in critically ill patients. The authors conclude that if for no other reason than the economic burden, prevention of bloodstream infections should be a key concern of hospitals. This reference does not describe the type of device or cleaning procedures as described in the current invention.

One reference, Cheung, G Y. and Otto, M. (2010) *Curr. Opin. Infect. Dis.* 23(3), 208-216 [7], describes the significant threat of catheter-related infections in neonatal patients, in particular that of *Staphylococcus epidermidis*. The puncturing of the skin is thought to be the predominant source of these catheter related infections. This reference does not describe the type of device or cleaning procedures as described in the current invention.

Other catheter cleaning methods have been described previously. One reference, Donlan, R. M. (2011) *Clin. Infect. Dis.* 52(8), 1038-1045 [8], examines the biofilm formation process and methods for prevention of biofilms. This reference states that biofilms often are able to withstand therapeutic levels of antibiotics, which may enable the bacteria in the biofilm to increase resistance to such antibiotics. The reference also discusses agents for the removal of such biofilms on medical devices including: chelating agents such as EDTA or sodium citrate (to remove calcium, magnesium, and iron), 70% ethanol solution (lock solution with or without additional antibiotic therapy), biofilm dispersant (oxidizing biocides, such as chlorine, surfactants, or enzymes, can also disrupt the biofilm and lead to cell detachment), or use of bacteriophages. The authors note that the biofilm dispersants have yet to have validated tests in humans. This reference does not describe the type of device or cleaning procedures as described in the current invention.

One reference, Vickery, K. et al. (2004) *Am. J. Infect. Control* 32(3), 170-176 [10], describes cleaning procedures tested for the ability to remove an *E. coli* biofilm from the surface of a lumen. The focus was on solutions with or without digestive enzymes and a detergent. The solutions with enzymes showed at best a 2-log reduction in bacteria, whereas the non-enzymatic solution "Matrix" killed 100% of the biofilm bacteria. The reference does not describe the multi-step cleaning method or the device as described in the current invention.

One reference, Kokai-kun, J. F. et al. "Enzyme Disruption of Bacterial Biofilms," U.S. Pat. No. 7,572,439 [11], describes the use of antibacterial enzymes to disrupt and kill biofilms in medical devices, including catheters. This reference also describes prophylactic administration of the antibacterial enzymes and enzyme based coatings of implanted medical devices. The reference particularly identifies lysostaplin as useful enzyme example. The reference states that the antibacterial enzymes can be co-administered, simultaneously or alternating, with other antimicrobial agents to more effectively disrupt the biofilm and prevent its reoccurrence. The antimicrobial agents describe include antibiotics. There are not multi-stage cleaning procedures or the specific device as described in the current invention.

One reference, Penna and Ferraz (2000) *Infect. Control Hosp. Epidemiol.* 21(8), 499-504 [12], describes cleaning procedures associated with medical equipment, including angiographic catheters. Previous cleaning procedures described include ethylene oxide for a long cycle (12-18 hours) or with hydrogen peroxide gas plasma for a short cycle (approximately 75 minutes). The new cleaning procedure presented for the catheters included: rinse with purified water, immersion and rinse with a hydrogen peroxide solution, soak in an enzymatic detergent, and rinse with purified water followed by drying with compressed air. The evaluation of the procedures used *Bacillus subtilis* spores. The authors note that their methodology would not fulfill the Food and Drug Administration (FDA) guidance document for ensuring sterilization. Given that major steps of the cleaning procedure are not included and the device design is different, this reference does not describe the type of device or cleaning procedures as described in the current invention.

One reference, Druce, J. D. et al. (2005) *Infect. Control Hosp. Epidemiol.* 26(8), 720-725 [13], describes non-lumen, multi-electrode catheters. The cleaning and sterilization protocols evaluated included: detergent treatment, enzyme cleaner treatment, ethylene oxide treatment, and a combination of the previous three treatments. These were assessed as to the removal of latent viruses, not bacterial biofilm. It should be noted that these devices were not treated while attached or within a patient. In comparison in patient treatment is considered one significant embodiment of the invention in the current invention. This reference does not describe the two-lined device or the specific multi-solution cleaning procedure described in the current invention.

Another reference, Betjes, M. G H. (2011) *Nature Reviews Nephrology* 7(5), 257-265 [6], describes a review of procedures regarding prevention of intraluminal contamination of the central venous catheter (CVC). Methods of proven efficacy in prevention include strict aseptic CVC insertion and handling protocols, use of chlorhexidine in alcohol solutions for skin cleansing, topical application of antimicrobial ointments, and antimicrobial lock solutions. The article even suggests CVC replacement as a viable option to prevent blood stream contamination by a biofilm. This reference does not describe the type of device or cleaning procedures as described in the current invention.

One reference, O'Grady, N. P. et al. (2011) *Clin. Infect. Dis.* 52(9), e162-e193 [14], includes various recommendations regarding prevention of catheter related infections. Among the most relevant to the invention described in the present invention is the recommendation of the use prophylactic antimicrobial lock solution in patients with long-term catheters who have a history of multiple CRBSI despite optimal maximal adherence to aseptic technique. The antibiotic lock is a highly concentrated antibiotic solution used to attempt to kill biofilms and other bacteria. General recommendations to avoid infections include replacement of catheters when possible rather than reuse. This reference does not describe the two-lined device or the multi-solution cleaning procedure described in the current invention.

In some embodiments, the current invention's device design is quite different than known devices. One reference, Dikeman, C. W. et al. European Patent Application EP1854502 B1 [15], describes a two-way valve inside each side of Y joint for an infusion catheter. The valves are pressure activated and do not require needles. These, however are described within the context of the reduction of blood clots and for ease of therapy rather than regarding reduction of device infection or removal of biofilm. This reference does not describe the two-lined device containing the microfluidic pressure switch, which operates as described in the current invention, or the specific multi-solution cleaning procedure described in the current invention.

One reference, Bergsneider, M. et al. United States Patent application publication number 20080281250 [16], describes various implanted medical devices, including catheters, with features that aim to reduce the accumulation of material within fluid conduits or interfaces. One of these features is a movable part, which sweeps, vibrates, or rotates in motion to remove materials. A magnetic actuator could move such a part. This reference does not describe the specific device features such as a flushing line or pressure switch of the device in Tab or cleaning procedures as described in the current invention.

One reference, Knox, S. J. and Schore, C. E. United States Patent application publication number 20070161949 [17], describes a catheter design in containing at least one filter there between, and a means for accessing negative pressure for creating a pressure associated with the distal end of the catheter tubing. The pressure differential prevents retrograde bacterial transmission thereby minimizing the likelihood of infecting the patient. While not limited to urinary catheters, the design provides significant advantages to catheter systems where drainage rather than input of fluid is desired. As it does not include the separate flushing line or pressure switch, this reference does not describe the type of device or cleaning procedures as described in the current invention.

One reference, Cosentino, L. C. et al. U.S. Pat. No. 4,721,123 [18], refers to a method and an apparatus for reprocessing catheters of the type having an inflatable balloon. The system described is used to clean then rinse used catheters for reprocessing. The catheters described here are not those envisioned by the current invention. This reference does not describe the type of device or cleaning procedures as described in the current invention.

One reference, Howell, G. H. et al. United States Patent Application 20110213340 [19], describes a device for and method of fluid infusion related to catheters. This reference does not describe the type of device or cleaning procedures as described in the current invention.

One reference, Zumeris, J. et al. U.S. Pat. No. 7,393,501 [20], describes a vibration based mechanical feature used to clear biofilms in catheters. This reference does not describe the two-lined device or the multi-solution cleaning procedure described in the current invention.

In one embodiment, the present invention contemplates a washable catheter affixed to a flushing line activated by a microfluidic pressure switch. In one embodiment, the catheter is designed to prevent bacteria/biofilm contamination without even a minimal introduction of contaminated fluids with bioactive agents into the blood stream of patients. In one embodiment, the catheter is designed to be reused. In one embodiment, a fluidic pressure switch is close to the distal end part of the catheter (line to subject) in proximity of the blood vessel. In one embodiment, when activated through the flushing line, the pressure switch closes access to the distal end of the catheter and allows the flow of fluid from the flushing line through into the central line. In one embodiment, cleaning reagents may then be used to eliminate any biofilm which may have developed in the catheter central line or flushing line. In one embodiment, the present invention contemplates a reagent kit designed for use with the catheter with the microfluidic pressure switch. In one embodiment, the reagents are able to detach cells and proteins attached to plastic surface better than pure bleach. In one embodiment, a specific protocol for cleaning that includes exposure to trypsin, a calcium deficient high ion concentration buffer, and 70% ethanol before flushing and normalization with saline solution.

REFERENCES

1. Hall-Stoodley, L. et al. (2004) "Bacterial biofilms: from the Natural environment to infectious diseases," *Nat. Rev. Microbiol.* 2(2), 95-108.
2. Maki, D. G et al. (2006) "The Risk of Bloodstream Infection in Adults With Different Intravascular Devices: A Systematic Review of 200 Published Prospective Studies," *Mayo Clin. Proc.* 81(9), 1159-1171.
3. Renaud, B. and Brun-Buisson, C. (2001) "Outcomes of Primary and Catheter-related Bacteremia: A Cohort and Case-Control Study in Critically Ill Patients," *Am. J. Respir. Crit. Care Med.* 163(7), 1584-1590.
4. Blot, S. I. et al. (2005) "Clinical and Economic Outcomes in Critically Ill Patients with Nosocomial Catheter-Related Bloodstream Infections," *Clin. Infect. Dis.* 41(11), 1591-1598.
5. Warren, D. K. et al. (2006) "Attributable cost of catheter-associated bloodstream infections among intensive care patients in a nonteaching hospital," *Critical Care Medicine* 34(8), 2084-2089.
6. Betjes, M. G H. (2011) "Prevention of catheter-related bloodstream infection in patients on hemodialysis," *Nature Reviews Nephrology* 7(5), 257-265.
7. Cheung, G. Y and Otto, M. (2010) "Understanding the significance of *Staphylococcus epidermidis* bacteremia in babies and children," *Curr Opin. Infect. Dis.* 23(3), 208-216.
8. Donlan, R. M. (2011) "Biofilm Elimination on Intravascular Catheters: Important Considerations for the Infectious Disease Practitioner," *Clin. Infect. Dis.* 52(8), 1038-1045.
9. Ouyang, Y. et al. (1997) "Visualization of the distribution of autophosphorylated calcium/calmodulin-dependent protein kinase II after tetanic stimulation in the CA1 area of the hippocampus," *J. Neurosci.* 17(14), 5416-5427.
10. Vickery, K. et al. (2004) "Removal of biofilm from endoscopes: evaluation of detergent efficiency," *Am. J. Infect. Control* 32(3), 170-176.
11. Kokai-kun, J. F. et al. "Enzyme disruption of bacterial biofilms," U.S. Pat. No. 7,572,439, application Ser. No. 10/401,342, filed Mar. 26, 2003. (issued Aug. 11, 2009).
12. Penna, T. C. V. P. and Ferraz, C. A. M. P. (2000) "Cleaning of Blood-Contaminated Reprocessed Angiographic Catheters and Spinal Needles," *Infect. Control Hosp. Epidemiol.* 21(8), 499-504.
13. Druce, J. D. et al. (2005) "Cleaning and Sterilization Protocol for Reused Cardiac Electrophysiology Catheters Inactivates Hepatitis and Coxsackie Viruses," *Infect. Control Hosp. Epidemiol.* 26(8), 720-725.
14. O'Grady, N. P. et al. (2011) "Guidelines for the Prevention of Intravascular Catheter-related Infections," *Clin. Infect. Dis.* 52(9), e162-e193.
15. Dikeman, C. W. et al. "Pressure actuated two-way valve for infusion catheter," European Patent Application EP1854502 B1, Application EP1547646A1, filed Dec. 22, 2003. (published Mar. 3, 2010).
16. Bergsneider, M. et al. "Self-Clearing Catheter for Clinical Implantation," United States Patent Application Publication Number 20080281250, application Ser. No. 11/919,936, filed May 10, 2006. (published Nov. 13, 2008).

17. Knox, S. J. and Schore, C. E. "Catheter system for minimizing retrograde bacterial transmission from a catheter tubing," United States Patent Application Publication Number 20070161949, application Ser. No. 11/327,835, filed Jan. 6, 2006. (published Jul. 12, 2007).
18. Cosentino, L. C. et al. "Catheter reprocessing system," U.S. Pat. No. 4,721,123, application Ser. No. 06/922,205, filed Oct. 23, 1986. (issued Jan. 26, 1988).
19. Howell, G H. et al. "Separatable Infusion Set with Cleanable Interface and Straight Line Attachment," United States Patent Application Publication Number 20110213340, application Ser. No. 12/736,678, filed May 13, 2009. (published Sep. 1, 2011).
20. Zumeris, J. et al. "Method, apparatus and system for treating biofilms associated with catheters" U.S. Pat. No. 7,393,501, application Ser. No. 10/445,956, filed May 28, 2003. (issued Jul. 1, 2008).

I claim:

1. An implantable medical device including a catheter, wherein said catheter comprises:
   a distal end,
   a central line connected to said distal end,
   a flushing line, and
      a valve comprised of a microfluidic movable pressure switch, said microfluidic movable pressure switch configured to move between said distal end and said flushing line, wherein the valve is configured so that when the microfluidic movable pressure switch is engaged to said flushing line, fluid flows from said central line to said distal end and when said microfluidic movable switch is engaged to said distal end, fluid flows from said flushing line to said central line, wherein said valve is attached within an end of said flushing line and said valve engages said central line with an external bracing structure;
   said microfluidic movable pressure switch is attached to a central rod disposed within at least one internal bracing feature;
   said microfluidic movable pressure switch attached to said central rod, wherein a tip of said microfluidic movable pressure switch is configured to block a narrowed portion of said central line on a tip of said catheter to prevent fluid flow.

2. The device of claim 1, wherein said catheter comprises a central venous catheter.

3. The device of claim 1, wherein said catheter comprises a urinary catheter.

4. A kit comprising:
   a plurality of cleaning reagents, said plurality of cleaning reagents comprising: a) digestive enzyme solution, b) calcium deficient buffer with high ion concentrations c) a solution comprising 70% ethanol, and d) physiological saline solution; a catheter comprised of:
   a distal end,
   a central line connected to said distal end,
   a flushing line, and
      a valve comprised of a microfluidic movable pressure switch, said microfluidic movable pressure switch is configured to move between said distal end and said flushing line, wherein said valve is configured so that when said microfluidic movable pressure switch is engaged to said flushing line, fluid flows from said central line to said distal end and when said microfluidic movable switch is engaged to said distal end, fluid flows from said flushing line to said central line wherein said valve is attached within an end of said flushing line and said valve engages said central line with an external bracing structure;
   said microfluidic movable pressure switch is attached to a central rod disposed within at least one internal bracing feature; said microfluidic movable pressure switch attached to said central rod, wherein a tip of said microfluidic movable pressure switch is configured to block a narrowed portion of said central line to prevent fluid flow.

5. The kit of claim 4, wherein said digestive enzyme solution contains trypsin.

6. The kit of claim 4, wherein said calcium deficient buffer with high ion concentration contains a chelating agent.

* * * * *